US 6,626,855 B1

(12) United States Patent
Weng et al.

(10) Patent No.: US 6,626,855 B1
(45) Date of Patent: Sep. 30, 2003

(54) CONTROLLED HIGH EFFICIENCY LESION FORMATION USING HIGH INTENSITY ULTRASOUND

(75) Inventors: Lee Weng, Bellevue, WA (US); David M. Perozek, Mercer Island, WA (US); Jimin Zhang, Bellevue, WA (US)

(73) Assignee: Therus Corpoation ( * ) Notice: Subject to any disclaimer, the term of this patent is extended or adjusted under 35 U.S.C. 154(b) by 136 days.

(21) Appl. No.: 09/721,526

(22) Filed: Nov. 22, 2000

Related U.S. Application Data
(60) Provisional application No. 60/167,707, filed on Nov. 26, 1999.

(51) Int. Cl.[7] ............................................. A61N 7/00
(52) U.S. Cl. ........................... 601/3; 600/439; 600/442; 601/2
(58) Field of Search .......................... 601/2, 3; 600/437, 600/438, 442

(56) References Cited

U.S. PATENT DOCUMENTS

| | | | | |
|---|---|---|---|---|
| 4,206,763 A | * | 6/1980 | Pedersen | 128/915 |
| 5,080,101 A | | 1/1992 | Dory | 128/660.03 |
| 5,080,102 A | | 1/1992 | Dory | 128/660.03 |
| 5,471,988 A | | 12/1995 | Fujio et al. | 128/660.03 |
| 5,492,126 A | | 2/1996 | Hennige et al. | 128/660.03 |
| 5,643,179 A | * | 7/1997 | Fujimoto | 601/2 |
| 5,666,954 A | | 9/1997 | Chapelon et al. | 128/660.03 |
| 5,697,897 A | | 12/1997 | Buchholtz et al. | 604/22 |
| 5,735,796 A | | 4/1998 | Granz et al. | 600/439 |
| 5,762,066 A | * | 6/1998 | Law et al. | 600/439 |
| 5,769,790 A | | 6/1998 | Watkins et al. | 600/439 |
| 5,788,636 A | | 8/1998 | Curley | 600/439 |
| 5,873,828 A | | 2/1999 | Fujio et al. | 600/439 |
| 5,904,659 A | * | 5/1999 | Duarte et al. | 601/2 |

OTHER PUBLICATIONS ter Haar, G., "Ultrasound Focal Beam Surgery," *Ultrasound in Medicine and Biology,* 1995, vol. 21, No. 9, pp. 1089–1100.

Sanghvi, N.T. and Hawes, R.H., "High–Intensity Focused Ultrasound," *Experimental and Investigational Endoscopy,* Apr. 1994, vol. 4, No. 2, pp. 383–395.

* cited by examiner

*Primary Examiner*—Marvin M. Lateef
*Assistant Examiner*—Runa Shoh Qaderi

(57) ABSTRACT

An ultrasound system used for both imaging and delivery high intensity ultrasound energy therapy to treatment sites and a method for treating tumors and other undesired tissue within a patient's body with an ultrasound device. The ultrasound device has an ultrasound transducer array disposed on a distal end of an elongate, relatively thin shaft. In one form of the invention, the transducer array is disposed within a liquid-filled elastomeric material that more effectively couples ultrasound energy into the tumor, that is directly contacted with the device. Using the device in a continuous wave mode, a necrotic zone of tissue having a desired size and shape (e.g., a necrotic volume selected to interrupt a blood supply to a tumor) can be created by controlling at least one of the f-number, duration, intensity, and direction of the ultrasound energy administered. This method speeds the therapy and avoids continuously pausing to enable intervening normal tissue to cool.

6 Claims, 10 Drawing Sheets

CONTROLLED HIGH EFFICIENCY LESION FORMATION USING HIGH INTENSITY ULTRASOUND

RELATED APPLICATIONS

This application is based on prior provisional patent application Ser. No. 60/167,707, filed on Nov. 26, 1999, the benefit of the filing date of which is hereby claimed under 35 U.S.C. §119(e).

FIELD OF THE INVENTION

This invention relates generally to methods and apparatus for efficiently heating biological tissues with high intensity ultrasound for therapeutic purposes, and in particular, to endoscopic devices for applying ultrasound energy to uterine fibroids and other pathologic tissues that are inside body or organ cavities, to destroy the tumor or the diseased tissue.

BACKGROUND OF THE INVENTION

Fibroids are benign tumors in women's uteri. There are different types of fibroids, including submucosal, which are inside the uterine cavity; intramural, which are in the uterine wall; and subserosal, which are outside the uterus. Fibroids may cause excessive bleeding and pain. For symptomatic fibroids, surgery is the predominate treatment. Every year in the U.S., there are more than 200,000 cases of fibroid-caused hysterectomies. To preserve the uterus, the patient may choose myomectomy, which removes the fibroids only. There are more than 80,000 abdominal myomectomies each year in the U.S. These surgical procedures cause significant trauma to the patients and result in significant costs. Consequently, patients need several days of hospital stay and suffer from the prolonged recovery.

Minimally invasive surgical (MIS) procedures have been explored to treat uterine fibroid trans-abdominally or transcervically under laparoscopic or hysteroscopic guidance. Many MIS apparatus have been developed to make the procedure less difficult. Several prior art devices are described in U.S. Pat. No. 5,304,124; U.S. Pat. No. 5,662,680; and U.S. Pat. No. 5,709,679. Besides surgically resecting and removing the tumor tissue, alternative treatments include using different energy forms, such as laser, radio frequency (RF), and cryo-therapy, to thermally ablate or necrose the fibroid tissue. Most of these techniques require the insertion of needles or other types of devices into the body of the fibroid. The mechanical damage to the fibroid and the uterus can cause bleeding during the treatment and adhesions after the treatment. Suturing the damage in the uterus is very difficult in the laparoscopic MIS procedure. Also, most of these alternative treatments are time consuming and technically challenging.

Uterine arterial embolization (UAE) has been investigated as an alternative treatment for uterine fibroids. In UAE, a catheter is inserted into the patient's femoral artery. The catheter is then advanced until its tip reaches the uterine artery. Many small particles are then injected into the uterine artery to block the blood flow. Both left and right uterine arteries are treated. Blood vessels supplying uterine fibroids are typically larger than the vessels in the normal uterine tissue. With properly sized particles, the blood vessels feeding the uterine fibroids are embolized, but not those in the normal uterine tissue. The fibroids then starve and die due to lack of a blood supply. The uterus survives, however, on the blood supplied from the ovarian artery and other collateral circulation. The embolization procedure may cause severe pain in the first few days after the treatment. Other disadvantages of UAE may include long X-ray radiation exposure during the procedure and other long-term potential adverse effects. The procedure is not recommended if the patient seeks a future pregnancy.

Ultrasound is a term that refers to acoustic waves having a frequency above the high limit of the human audible range (i.e., above 20 KHz). Ultrasound waves have the capability of penetrating into the human body. Based on this property, ultrasound in the frequency range of 2–20 MHz has been widely used to image internal human organs for diagnostic purposes. Ultrasound imaging has also been suggested as a tool for guidance during a resectoscopic surgery (U.S. Pat. No. 5,957,849).

When ultrasound energy is absorbed by tissue, it becomes thermal energy, raising the temperature of the tissue. To avoid thermal damage to tissue, the power level in diagnostic ultrasound imaging is kept very low. The typical ultrasound intensity (power per unit area) used in imaging is less than 0.1 watt per square centimeter. High intensity focused ultrasound, which can have an intensity above 1000 watts per square centimeter, can raise the tissue temperature at the region of the spatial focus to above 60–80 degrees Celsius in a few seconds and can cause tissue necrosis almost instantaneously.

High intensity ultrasound has been proposed to treat and destroy tissues in the liver (G. ter Haar, "Ultrasound Focal Beam Surgery," Ultrasound in Medicine and Biology, Vol. 21, No. 9, pp.1089–1100, 1995); in the prostate (N. T. Sanghvi and R. H. Hawes, "High-intensity Focused Ultrasound," Experimental and Investigational Endoscopy, Vol. 4, No. 2, pp.383–395, 1994); and in other organs. In U.S. Pat. Nos. 5,080,101, 5,080,102, 5,735,796, 5,769,790, and 5,788,636, for example, ultrasound imaging is combined with a high intensity ultrasound treatment to target the treatment region and to monitor the treatment process. In U.S. Pat. Nos. 5,471,988, 5,492,126, 5,666,954, 5,697,897, and 5,873,828, endoscopic ultrasound devices with both imaging and therapeutic capabilities are disclosed. These devices all have an elongated tube or shaft, so that they can be inserted in organ cavities (e.g., into the rectum) or into the abdominal cavity through a puncture hole in the abdominal wall to bring the ultrasound imaging and treatment sources closer to the disease sites. Some of them have flexible ends, which can be bent to fit the anatomy of a specific patient.

The therapeutic ultrasound beam is focused inside tissue to a small spot of a few millimeters in size. At the focus, tissue temperature rapidly exceeds a level sufficient to cause tissue necrosis, thus achieving the desired therapeutic effect. Outside of the focus, ultrasound energy is less concentrated, tissue temperature rise remains below the necrosis level during the typically short exposure times employed. To treat a tissue volume larger than the focal spot, in the prior art, the ultrasound focus is deflected mechanically or electronically to scan, or incrementally expose, the target tissue volume. One disadvantage of the current high intensity ultrasound therapy is its inefficiency when treating large tumors or heating a large volume of tissue. Even though a three-second ultrasound pulse can increase the temperature of tissue at its focus dramatically, the ultrasound treatment must typically pause 40–60 seconds between two subsequent pulses to allow the intermediate tissue between the focus and the ultrasound transducer to cool sufficiently to avoid thermally damaging the tissue. The volume of tissue necrosis for each treatment pulse is very small (~0.05 cm$^3$). For example, to treat a volume of tissue within a 3 cm diameter sphere, it will take more than 4 hours, too long to be practical in most clinical situations. Many symptomatic uterine fibroids are larger than 2–3 cm in diameter, and multiple fibroids are also common. To be acceptable for clinicians and patients, the ultrasound treatment time must be significantly reduced.

Large device size is the second disadvantage of the therapeutic ultrasound apparatus in much of the prior art. Most of these devices have two separated ultrasound transducers, including one for imaging and the other for therapy. For effective treatment, the diameter of the treatment transducer is approximately equal to the maximum depth, where the f-number (transducer diameter divided by its focal length) of the transducer is about one (f/1). The transducer surface area must also be sufficiently large to generate high ultrasound power. In some prior art endoscopic devices (for example, in U.S. Pat. Nos. 5,471,988 and 5,873,828), there is a large orifice in the center of the therapy transducer for positioning an imaging transducer. This orifice reduces the area of the treatment transducer and increases its effective f-number. In this case, the size of the treatment transducer must be increased to maintain its effectiveness, so that the overall dimensions of the device are increased. For endoscopic (trans-cervical or trans-abdominal) uterine fibroid treatments, the maximum acceptable diameter of an ultrasound device is about 10 mm. It is seen that it is very difficult to meet this requirement with the large two-transducer configuration.

There is another disadvantage of the two-transducer configuration in which there is an orifice in the center of the treatment transducer. In endoscopic uterine fibroid treatment, the ultrasound device is directly brought against the surface of the fibroid tumor. The tumor surface near the orifice of the transducer will not be treated unless the transducer is moved away or aside from its initial position. Oftentimes, the space is very limited, especially inside the uterus. There may not be sufficient space to permit the device to move, a limitation that results in incomplete treatment of the tumor.

What is needed is a minimally invasive or noninvasive device for treating uterine fibroids. The device should preferably cause minimal or no trauma to the patient body so that the patient requires minimum or no recovery time; it should be easy to use; and, the treatment should be quickly administered. The device should preferably not cause blood loss during the treatment procedure; it should not mechanically damage the treated organ (e.g. uterus) to avoid the need for complicated organ repair (such as suturing or extensive cauterization); and, it should not increase the risk of post-operative adhesions and other complications. In addition, the device should be capable of carrying out the following functions:

(1) Ultrasonically increase the tissue temperature in the uterine fibroid to cause tumor necrosis. Shrinkage of the necrosed tissue will reduce the blood supply to the tumor. This occlusion effect will further reduce the chance of survival for the tumor.

(2) Significantly reduce the ultrasound treatment time and thereby improve physician and patient acceptance. A positive feedback heating process can be provided to efficiently and rapidly raise the temperature in a large volume of tissue.

(3) Combine the ultrasound imaging and therapy transducer in one to enable the -dimensions of the apparatus to be more compact so that the device can be inserted into patient's uterine cavity or permit practical laparoscopic use (e.g., be inserted trans-abdominally).

(4) Include a treatment transducer that does not have an orifice in its center, so that the tumor tissue can be treated thoroughly.

(5) Provide ultrasound imaging capability for treatment guidance. The imaging capability should provide real-time assessment of the anatomy before, during, and after the treatment. Doppler imaging can be advantageously employed to aid targeting and the assessment of treatment.

(6) Use ultrasound to detect and differentiate the tissue property changes before and after the treatment to make an assessment of the treatment result possible.

(7) Create an acoustic absorption barrier inside the treated tissue to prevent the tissue beyond the desired treatment zone from being thermally damaged.

(8) Provide a feedback control mechanism to turn the treatment transducer element off when the transducer is not properly coupled to the tissue to prevent the device from being damaged by reflected ultrasound power.

(9) Provide an effective cooling mechanism to prevent the device from being thermally damaged.

(10) Use an ultrasound contrast agent (micro-bubbles) to enhance the treatment effect.

(11) Provide effective means to acoustically couple an ultrasound source to targeted tissue structures.

(12) Use elasticity imaging to assess the state of tissues prior, during, and after ultrasonic treatment.

(13) Employ cavitation as a therapeutic means to necrose selected tissues.

Currently, an endoscopic ultrasound probe is not available that can provide the above-noted functions. Accordingly, it will be apparent that both such a device and an effective and efficient method for treating uterine fibroid tumors and other internal tissues and diseased tissue masses is needed that overcomes the problems with prior art apparatus and methods.

SUMMARY OF THE INVENTION

The present invention is directed to a method and apparatus for efficiently treating uterine fibroids and other diseases with high intensity ultrasound, where the apparatus is small enough to fit in the limited space in a patient organ cavity or a limited puncture size on an abdominal wall.

Specifically, an ultrasonic system for destroying undesired tissue at an internal site within a body of a patient includes a probe that is sized to be inserted within a body of a patient. An ultrasonic transducer is mounted proximate a distal end of the probe and is adapted to couple to a power supply used to selectively energize the ultrasonic transducer so that it produces a focused beam of high intensity ultrasonic energy. An ultrasound transmissive interface is coupled to the distal end of the probe and is disposed and adapted to conform to a surface of the undesired tissue. The interface provides a liquid layer that more efficiently transmits the high intensity ultrasonic energy produced by the ultrasonic transducer into the undesired tissue. The high intensity ultrasonic energy increases a temperature of the undesired tissue sufficiently to cause the tissue to necrose.

In one form of the invention, the ultrasound transmissive interface comprises an elastomeric cavity that is adapted to contain a liquid. The elastomeric cavity is disposed between the ultrasonic transducer and the surface of the undesired tissue so that the high intensity ultrasonic energy passes through the liquid within the elastomeric cavity and into the undesired tissue. The elastomeric cavity is formed at least in part from a semi-permeable membrane, so that the liquid from within the elastomeric cavity weeps onto a surface of undesired tissue to increase the efficiency with which the high intensity ultrasonic energy is coupled into the undesired tissue.

In another form of the present invention, the ultrasound transmissive interface comprises a cap made of an elastomeric material, which is disposed to surround the ultrasonic transducer. The cap is adapted to seal against the undesired tissue and to contain a liquid that increases an efficiency with which the high intensity ultrasonic energy is coupled into the undesired tissue. In addition, the cap preferably includes a rim having a double lip seal formed around a perimeter. A passage in the cap is adapted to couple the double lip seal to a vacuum line so that the rim of the cap is held against a surface of the undesirable tissue, sealing the liquid inside of the cap.

Another aspect of the present invention is directed to a method for administering an ultrasonic therapy to destroy at least a portion of an undesired tissue mass. The method includes the steps of providing an ultrasonic transducer that emits a focused high energy ultrasonic energy when energized, and positioning the ultrasonic transducer proximate the undesired tissue mass. The ultrasonic transducer is directed toward a desired focal point within the undesired tissue mass. Then, the ultrasonic transducer is energized so that it emits the focused high energy ultrasonic energy at the desired focal point, causing necrosis of a portion of the undesired tissue mass disposed at the desired focal point. At least one of an f-number, an intensity, a time, and a direction of the high intensity ultrasonic energy emitted into the undesired tissue mass is controlled to achieve a desired shape and size of a necrotic zone of undesired tissue, destroyed as a result of being heated by the high intensity ultrasonic energy. The necrotic zone substantially blocks the high intensity ultrasonic energy from penetrating beyond the necrotic zone. The desired shape and size of the necrotic zone are preferably selected and formed so as to cause substantially all of the undesired tissue mass to ultimately be destroyed.

The step of controlling preferably includes the step of repositioning the ultrasonic transducer to direct the high intensity ultrasonic energy at a different portion of the undesired tissue mass, to achieve the desired shape and size of the necrotic zone. In one application of the method, the desired shape and size of the necrotic zone are selected so that formation of the necrotic zone substantially deprives the undesired tissue mass of a blood supply, causing the ultimate destruction of the undesired tissue mass. In another application of the method, the desired shape and size of the necrotic zone are selected to control bleeding at a treatment site.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the following description of the present invention, its application in treating uterine fibroid tumors is discuss in some detail. However, it should be emphasized that the device and methods described herein may also be used to apply ultrasound therapy treatment to other organ systems, lesions, and disease states. The therapy delivered may be thermal ablation, where a temperature rise is established to a level at which tissues are no longer viable; mechanical ablation, where cavitation is employed as the primary ablative means; or may achieve hemostasis wherein bleeding or blood flow in intact organs is arrested. Such applications of the present invention may be accomplished in open, invasive surgery, by way of established minimally invasive techniques (for example, by way of body entry through one or more small incisions or punctures), or in some cases, noninvasively, through the skin surface or through the linings of body cavities such as the rectum, vagina, or esophagus. Ablative treatment with the present invention may be applied to a wide range of benign or cancerous lesions of the liver, kidney, pancreas, spleen, prostate, breast, bowel, rectum or similar organ systems, wherein the device described herein may be placed in close proximity to the disease location. Also, acoustic hemostasis treatment may be employed to deprive a disease lesion of its blood supply or used to facilitate surgical procedures by arresting bleeding or blood flow.

Many tumors, such as uterine fibroids, locate superficially inside or outside the organ. During hysteroscopic or laparoscopic surgeries, surgeons can easily reach the surfaces of those tumors with an intra-cervical or intra-abdominal instrument. For an ultrasound transducer at the tip of the intra-cavity instrument touching the tumor directly, there will be little or no intermediate tissue that needs to be spared and cooled, so that pauses in the treatment for this purpose may become unnecessary.

Figure 1:
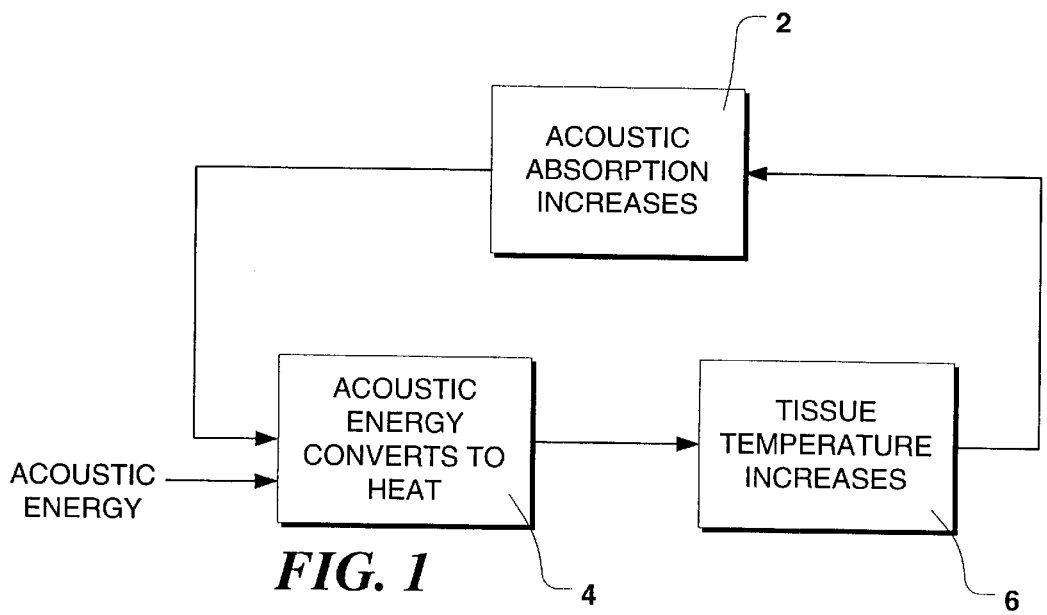
FIG. 1 is a block diagram of the positive feedback mechanism of the improved tissue heating process.
Figure 2A:
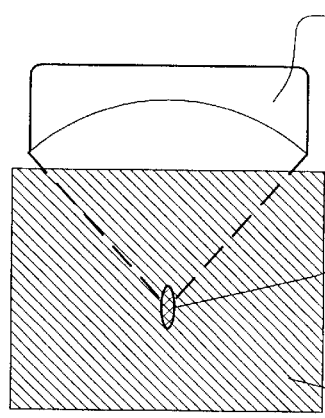
FIGS. 2A–2D illustrate different thermal lesion shapes.
Figure 2B:
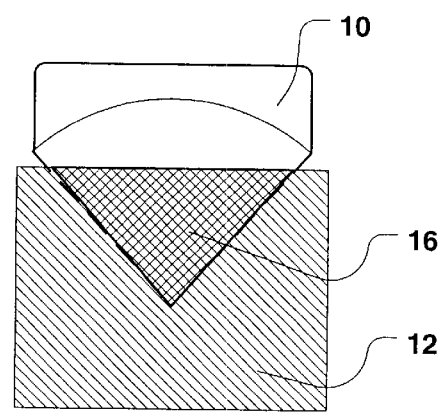

According to conventional wisdom, the pre-focal heating is considered to be a negative effect and needs to be minimized. In the case of intra-cavity treatment of uterine fibroids, however, this pre-focal heating can provide significant enhancement to the efficiency of tissue heating when the ultrasound transducer can be disposed in close contact with the tumor surface. A positive feedback mechanism of tissue heating (illustrated in FIG. 1) is preferably used to improve the efficiency of the treatment provided by the present invention. The positive feedback indicated by a block 2 of FIG. 1 enhances acoustic absorption. The acoustic energy is converted to heat, as noted in a block 4, resulting in a greater temperature rise in the tissue, as indicated in a block 6. Tissue acoustic absorption increases significantly when its temperature rises above 50° C. Referencing FIG. 2A, a small f-number, high intensity ultrasound transducer 10, running in continuous-wave (CW) mode, raises the temperature in tissue 12 at its focus to 70–90° C. in less than two seconds and forms a small lesion 14. This isolated thermal lesion serves two purposes. First, it is the initial seed to start the positive feedback heating process; and, secondly, its high acoustic absorption blocks ultrasound energy from penetrating beyond the focal depth to cause undesirable damage to normal tissue. In an experimental study, it was observed that after the lesion started at the focus, it first grew along the central axis of the transducer and towards the transducer to form an elongate lesion. Then, the end of the elongate lesion closer to transducer began growing laterally wider. Eventually, the lesion became a wedge shape 16 (FIG. 2B). The tissue layer near the surface, adjacent to the transducer 10, was the last portion to necrose.

In an experimental study, a wedge-shaped lesion of tissue necrosis was generated with this mechanism by running the ultrasound power continuously, while keeping the transducer position fixed. The volume of the thermal lesion was about 4.5 cm$^3$, and the treatment time was approximately two minutes. The average treatment rate was about 2.25 cm$^3$/min, which was 45 times faster than provided by a conventional pulse-pause treatment strategy.

Figure 2C:
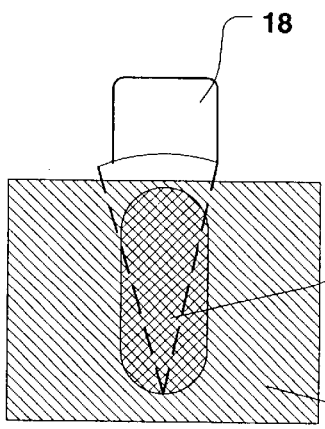
Figure 2D:
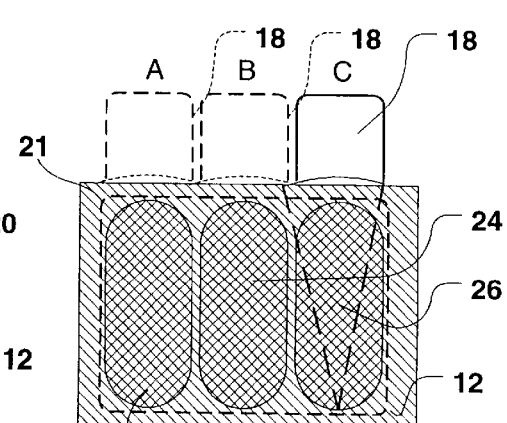

Using the present invention, the size and the shape of the large thermal lesion can be readily controlled. To form a thin elongate lesion column 20 in the tissue (FIG. 2C), a circular transducer 18 with a relatively large f-number (~2) is used to treat the tissue over a relatively short time. To create a conical shaped lesion, a circular transducer with a small f-number (~1) is used to treat the tissue for a relatively long time. To form a thin, wedge-shaped lesion, i.e., shaped like a slice of pie (FIG. 2B), a cylindrical or truncated circular transducer is used to treat the tissue over a relatively long time. A generally rectangular lesion plane 21 (FIG. 2D) can be generated by forming a row of tightly spaced lesion columns 22, 24, and 26. Each column is formed from a fixed transducer position in a short time. The transducer may then be quickly shifted laterally to generate the next adjacent column, moving from position "A" to "B" to "C" as shown in FIG. 2D. Thermal diffusion in the tissue fuses the columns together to form rectangular lesion plane 21. It is also possible to create a large lesion in the tissue without damaging the organ surface. One approach is to cool the tissue surface with circulating water or saline. The other approach is to use an attenuation measurement technique described below, to monitor lesion progress (growth) and control power, accordingly.

Figure 3A:
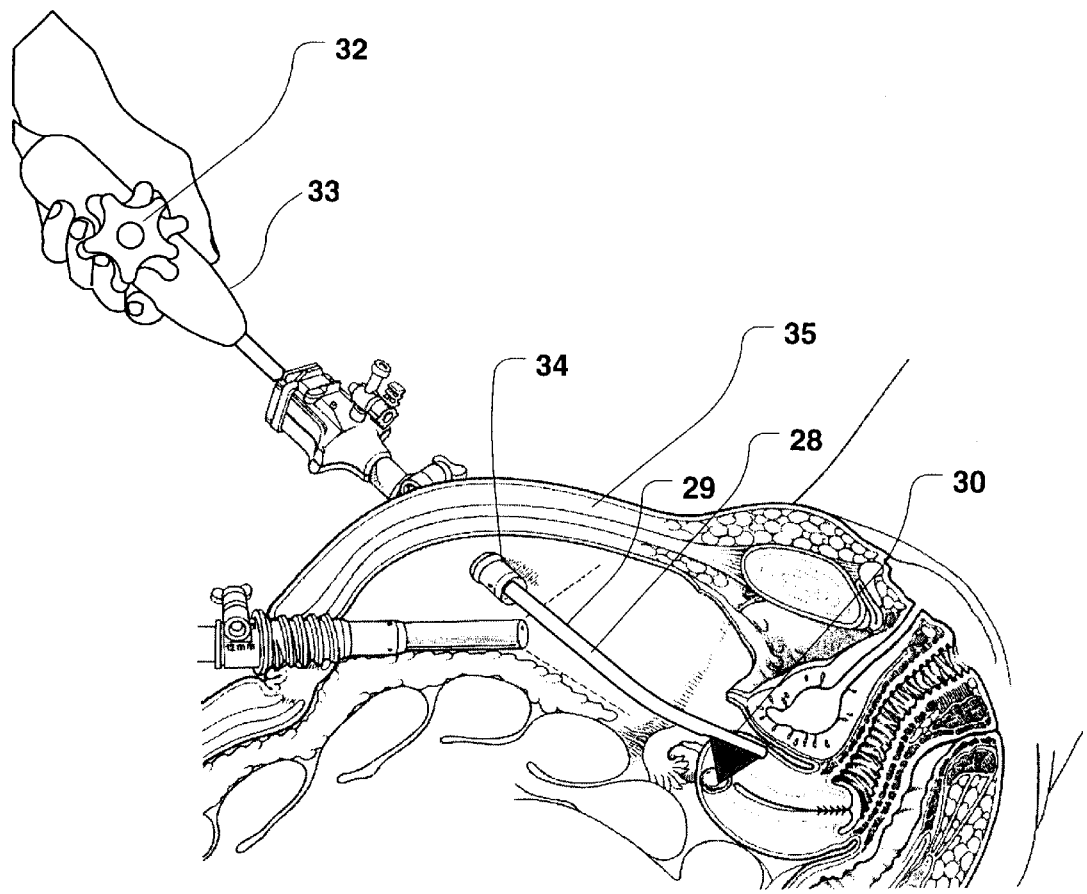
FIG. 3A is a cross-sectional view of a portion of a patient's body, illustrating application of an endoscopic device in accord with the present invention, which can both acquire ultrasound images and generate high intensity therapeutic ultrasound at its distal end.
Figure 3B:
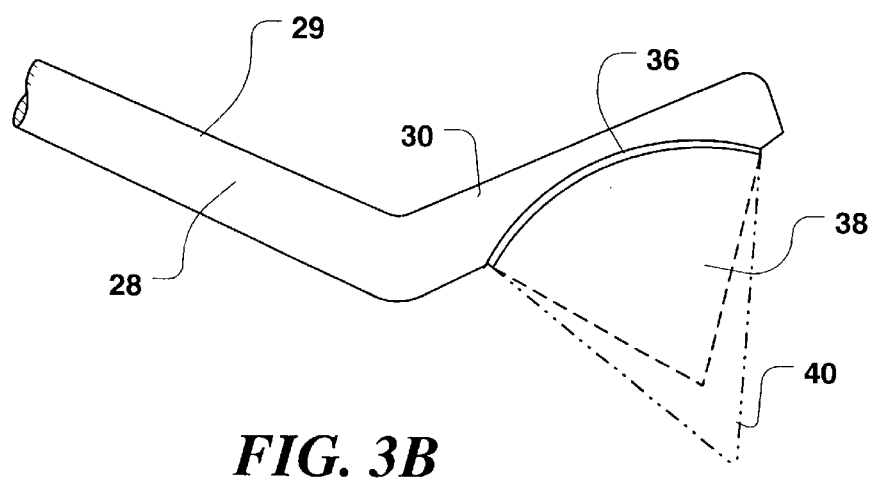
FIGS. 3B and 3C are side elevational views of a portion of the device shown in FIG. 3A, illustrating an imaging field and a treatment field of the device.

The basic concept and configuration of a high intensity ultrasound device 29 in accord with the present invention are shown in FIGS. 3A and 3B. The device has a thin, elongate shaft 28 that can be inserted through the cervix into the uterine cavity, or, as shown in FIG. 3A, through a laparoscopic opening 34 in the abdominal wall and into the abdominal cavity. A distal end 30 of the shaft contains a concave-shaped ultrasound transducer array 36 (FIG. 3B) and may be formed into different curves to fit different anatomies of individual patients. The distal end that is thus formed can be permanently fixed or articulated by turning a control knob 32 on a handle 33 of the device. Transducer array 36 in FIG. 3B is operable for both ultrasound imaging and treatment. To form an ultrasound image, the transducer array generates ultrasound pulses and receives echoes from the imaged anatomy in a cross-sectional area 40. The two-dimensional (2D) ultrasound image displays the cross-sectional view of the anatomy. The image can be updated rapidly in real-time with a frame rate of, for example, 10–30 frames per second. Physicians can then view this real-time image to locate the tumor or other tissue that needs to be treated or spared from treatment. When the treatment area is identified in the image, the transducer array is employed to generate high intensity ultrasound focused in a treatment area 38. After the tissue in the treatment area has been necrosed, the distal end of the ultrasound device is moved to a new location to sequentially treat another part of the tumor tissue. The imaging and the treatment are interleaved in time so that the treatment process and the progress of the treatment may be monitored.

Doppler flow imaging (spectral Doppler or power mode Doppler) may be utilized to assist targeting and to monitor treatment effects and to determine the endpoint of the therapy. Imaging blood flow is particularly useful when a blood flow occlusion strategy is being utilized, since the cessation of blood flow can be directly monitored. Doppler imaging facilitates localization of the vascularity typically surrounding uterine fibroid tumors or other tumor masses.

There are many possible combinations of the imaging and treatment capabilities. Imaging and therapy may be one-, two-, or three-dimensional in various combinations; scan geometries may be fixed or selectable; and imaging and therapy may proceed either simultaneously or sequentially in time. A preferred embodiment of the ultrasound intra-cavity device discussed herein has the capability to carryout 2D real-time imaging and the capability to produce tissue necrosis in a substantially 2D slice (thickness of this slice is nominally less than one centimeter). Including the lesion-control techniques discussed above, there are many ways to control treatment geometry with this device. Different spatial beam patterns can be generated from by the ultrasound transducer array included on the device to form a specific lesion shape, or potentially, to reduce treatment time. Multiple sequential exposures of different spatial beam patterns can also be used to control the treatment dosage at different locations to form lesion shapes that cannot be generated by fixed beam patterns.

Figure 6:
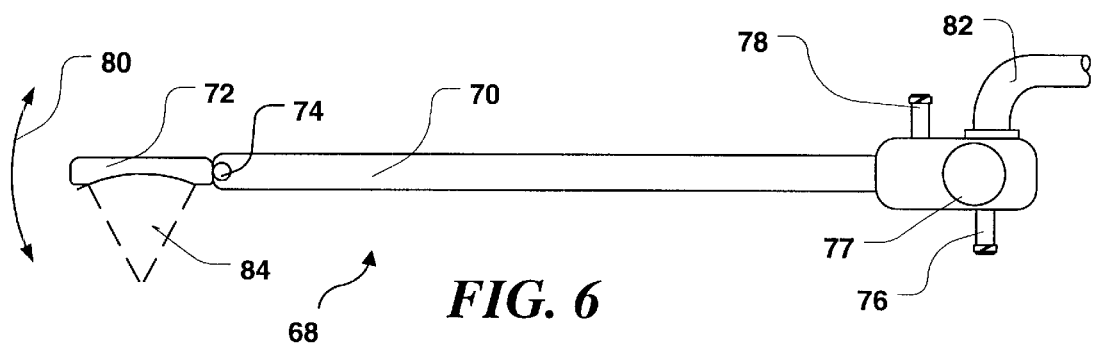
FIG. 6 is a schematic diagram of the trans-cervical ultrasound device with an articulated end.

As shown in FIG. 6, a trans-cervical ultrasound device 68 is adapted to treat submucosal fibroids. The device is inserted into a patient's uterine cavity through the vagina and the cervical canal. The uterine cavity is distended with sterile water or saline under 50–80 mm Hg pressure delivered through internal channels inside a shaft 70 of the device and connected to couplings 78 and 76. The water provides working space for manipulation of the device, and the water thus infused also serves as a transducer coupling and cooling medium.

The fibroid is visualized by ultrasound imaging using trans-cervical ultrasound device 68. As a function of the tumor size and shape, the physician selects the appropriate treatment geometry and turns the therapeutic ultrasound power on to necrose a slice volume of the tumor tissue in front of the transducer. The entire tumor is then treated typically piece by piece. During the treatment, the transducer (not separately shown) at a distal end 72 of the device does not have to directly contact the tumor surface—the water in the uterus is a good acoustic coupling and transmission medium. After the tumor is completely treated, the physician removes the device and drains the water from the patient's uterus. The procedure is finished without any surgical invasion to the tissue.

Figure 7A:
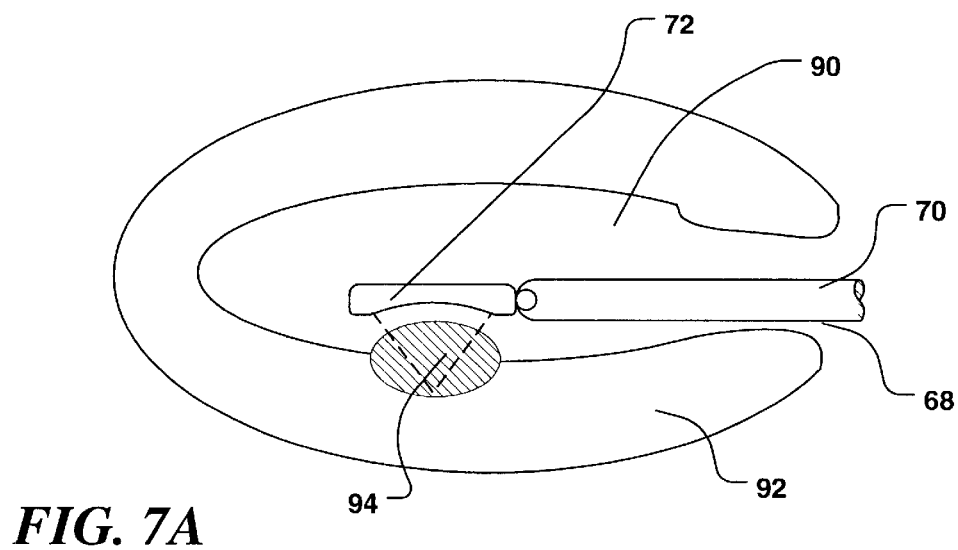
FIGS. 7A and 7B are schematic diagrams showing transcervical hemostasis treatment performed in combination with resectoscopic removal of submucosal fibroids.
Figure 7B:
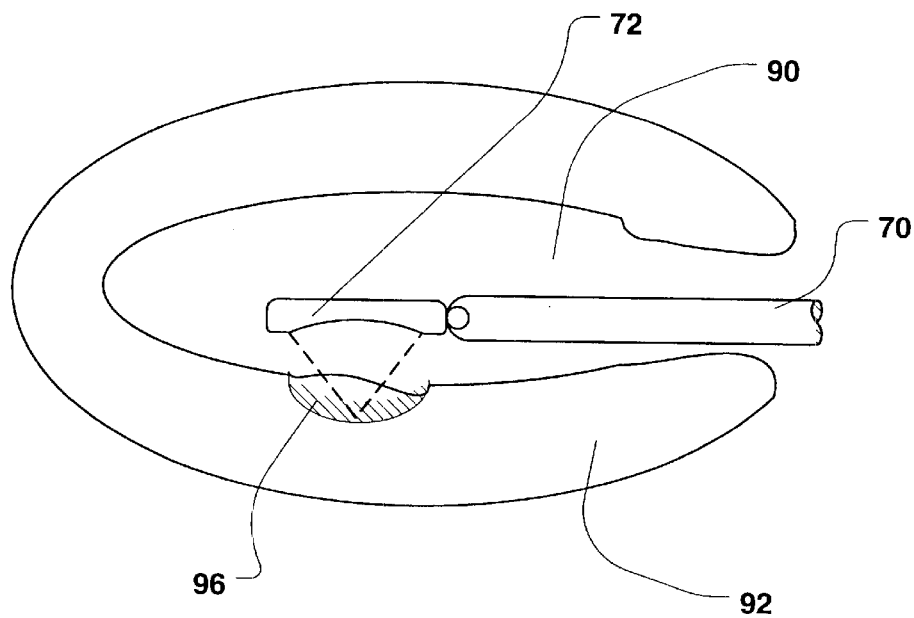

There are two possible approaches for providing treatment of a submucosal fibroid tumor 94 with trans-cervical ultrasound device 68. The physician can treat the whole tumor directly with the ultrasound device, as shown in FIG. 7A, or treat only a remaining tumor base 96, as shown in FIG. 7B, after a portion of the tumor is removed by using a resectoscope. In FIG. 7A the transducer in distal end 72 is placed adjacent to tumor 94 inside a water-filled uterine cavity 90. For the latter approach, the ultrasound device works not only as an ablation tool, but also as a hemostasis tool to seal off the open, bleeding vessels around and inside the exposed tumor base.

Figure 8A:
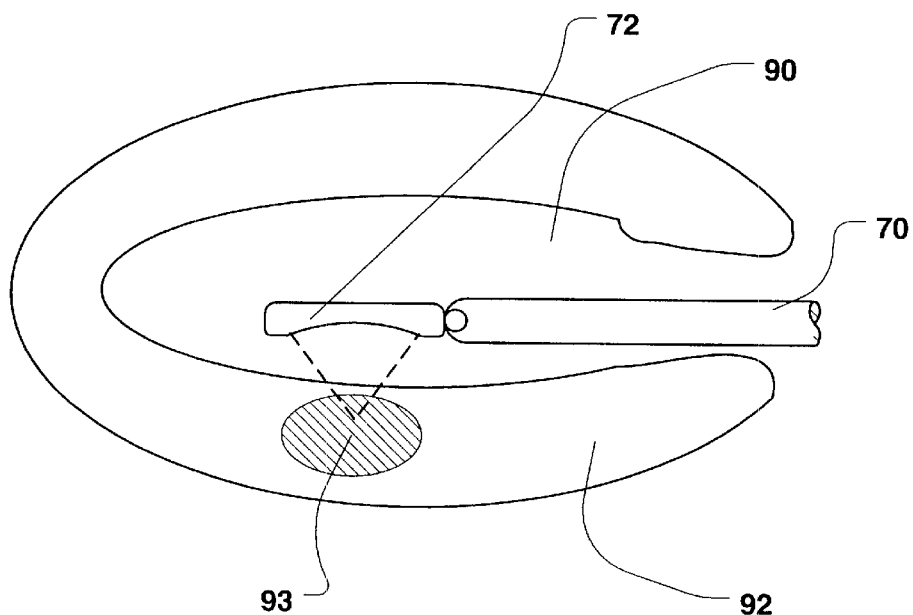
FIGS. 8A and 8B are schematic diagrams respectively showing the trans-cervical and the trans-abdominal ultrasound device treating intramural fibroids from inside and from outside of the uterus.
Figure 8B:
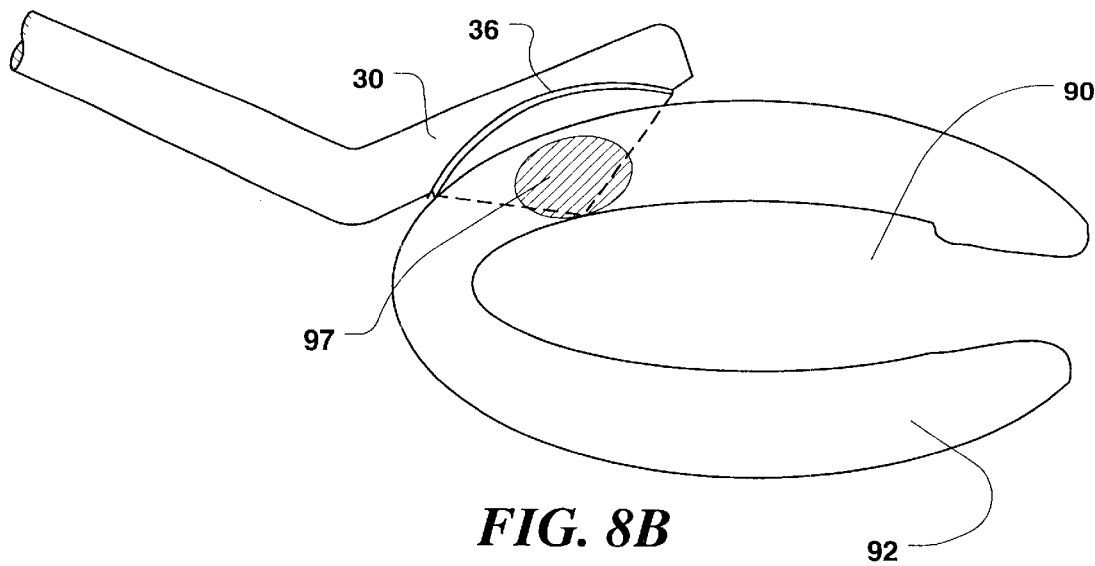

A similar technique may be used to treat intramural fibroids as illustrated in FIGS. 8A and 8B. If a tumor 93 is closer to the inside of the uterus (FIG. 8A), a trans-cervical ultrasound device is the choice for the treatment. Otherwise, a trans-abdominal device may be used (FIG. 8B). Some intramural fibroids 96 are imbedded inside normal uterine tissue, e.g., in a uterine wall 92. The physician may want only to necrose the tumor but not the uterine wall that covers the tumor. In this case, the physician can use the lesion geometry control techniques described above to heat only the tumor inside the uterine wall without thermally damaging the surrounding tissue.

Figure 9A:
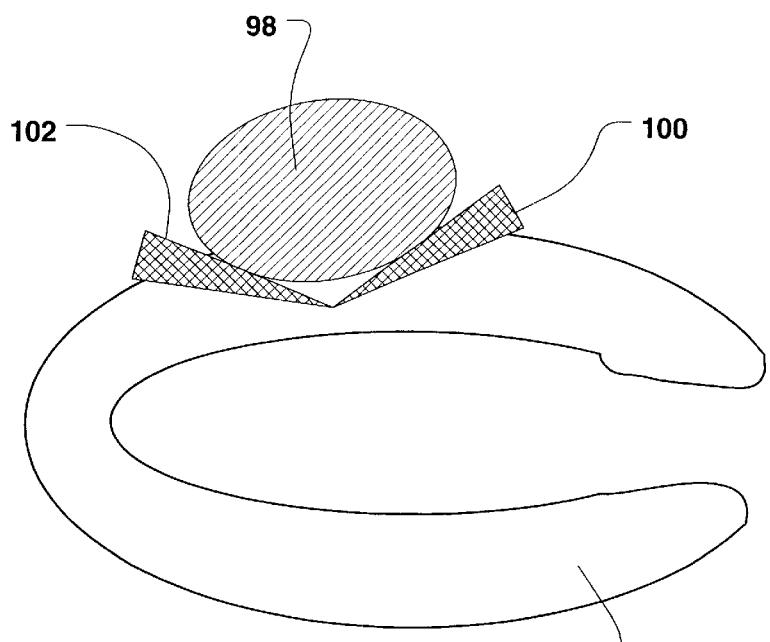
FIGS. 9A and 9B are schematic diagrams respectively showing laparoscopic occlusion treatment of subserosal fibroids, and a wedge of necrosed tissue produced thereby.
Figure 9B:
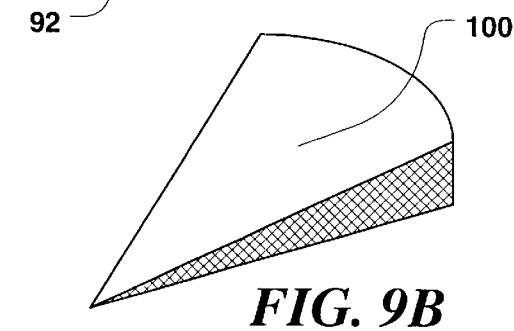

Subserosal fibroids are disposed substantially outside of the uterus. When these are symptomatic, they may be larger than submucosal and intramural fibroids. However, the trans-abdominal ultrasound device according to the present invention can also be used to treat them. If the physician uses the same treatment technique as described above to thermally necrose the entire tumor, it will take longer time, because they are relatively large. An alternative approach is shown in FIGS. 9A and 9B, where only the tumor base is treated by a series of sectors, or pie-shaped applications 100, 102 (FIG. 9B) that are circumferentially disposed around the base of a tumor 98. After the entire tumor base is heated sector by sector, the tumor tissue in the base shrinks. The tissue shrinkage occludes blood vessels in the base and achieves effective tumor starvation as oxygen and nutrient supplies are interrupted. Without a blood supply, the tumor will die. The necrosed tumor will then shrink in volume, so that the pressure symptoms experienced by the patient due to the growth of the tumor will be relieved.

Figure 10:
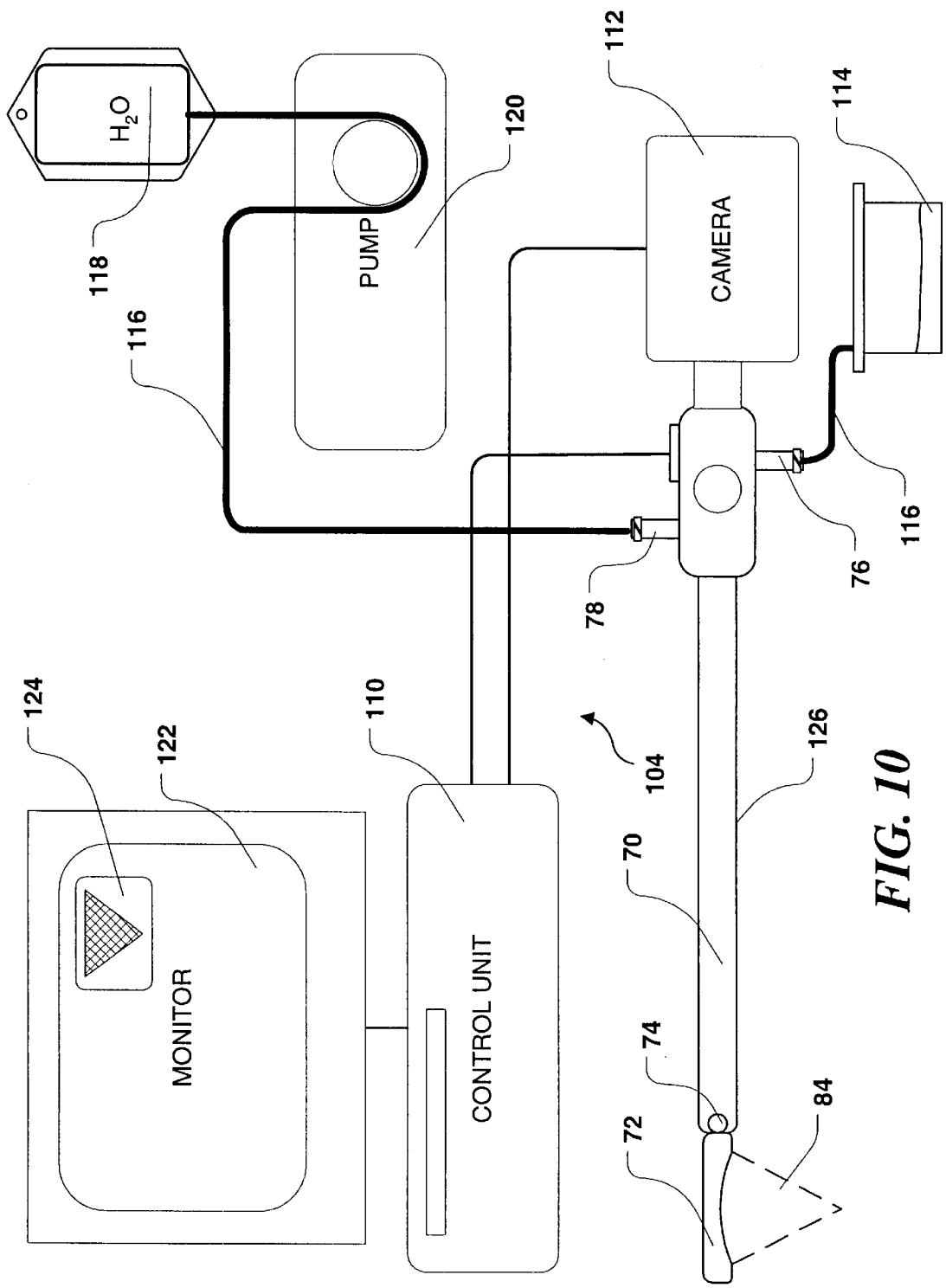
FIG. 10 is a block diagram of the trans-cervical ultrasound device connected with its control unit, display, and fluid management unit.

A system 104 that supports operation of trans-cervical ultrasound device 68 is shown in FIG. 10. The system consists includes one or more ultrasound applicators 126, an optional optical hysteroscope (not separately shown), which is inside the applicator, and its associated camera 112, a treatment control unit 110, a TV monitor 122, and a fluid management system that includes a fluid management system pump 120, tubing 116, and a waste collection container 114. The hysteroscope, camera, monitor, and fluid management system are typically available in a well-equipped gynecology operating room. The optional hysteroscope may be useful for visually locating the tumor. Control unit 110 provides electronic signals and power to the ultrasound transducer for both imaging and therapy. The ultrasonic image and the optical image from the camera attached to the hysteroscope are combined in the control unit and are preferably displayed on the monitor in a "picture-in-a-picture" format 124. Alternatively, either one of the images may be displayed alone. Fluid management system pump 120 controls the saline or water pressure and the flow rate into the uterus.

Different configurations of the trans-cervical ultrasound device shown in FIG. 6 have specific advantages. They all have two irrigation channels for fluid in and out, one electrical cable to connect to the control unit, and one utility channel for the hysteroscope. The difference is in their tip configuration. In FIG. 6, the distal end of the applicator can bend to different angles 80 about a pivot 74, to accommodate different approaches to the treatment zone. A knob 77 at the device handle controls the tip articulation, providing an adjustable head angle over a range of up to 90 degrees. Alternatively, the distal end of the device may be fixed, and several applicators of different fixed tip angles can be provided for different treatments.

The ultrasound transducer in the end of the trans-cervical applicator may have a limited usable lifetime. The tip of the device may be a reposable (disposable, with a limited number of times of reuse). A used tip can thus be removed, and a new tip attached. The reposable portion may include shaft 70, so that the connection port will be in the handle, which stays outside the patient and is not immersed in fluid.

Figure 3C:
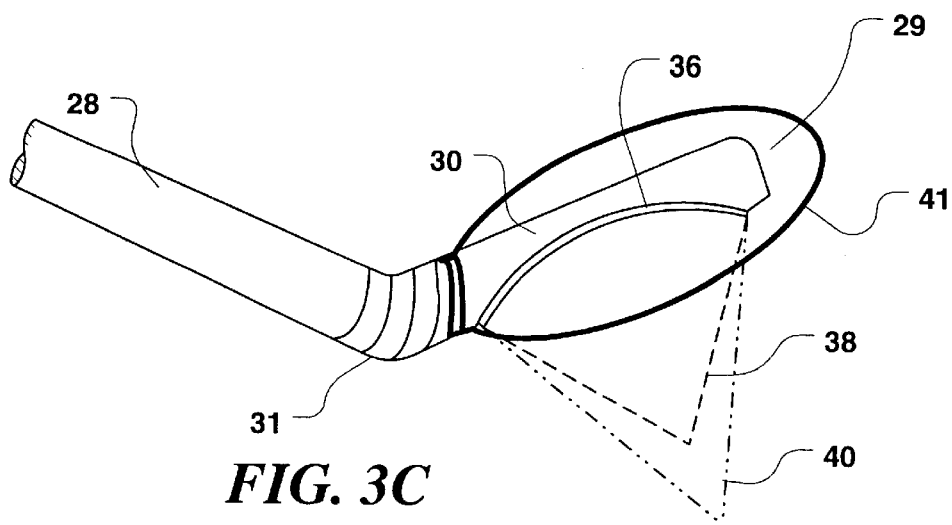
Figure 4A:
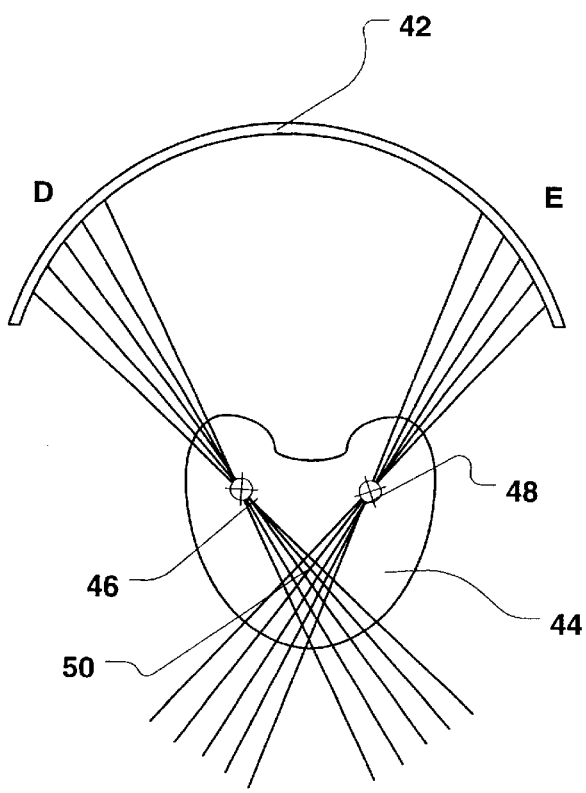
FIGS. 4A and 4B are schematic diagrams of different treatment beam forming techniques used to control the lesion geometry and illustrating spatial lesion formation.
Figure 4B:
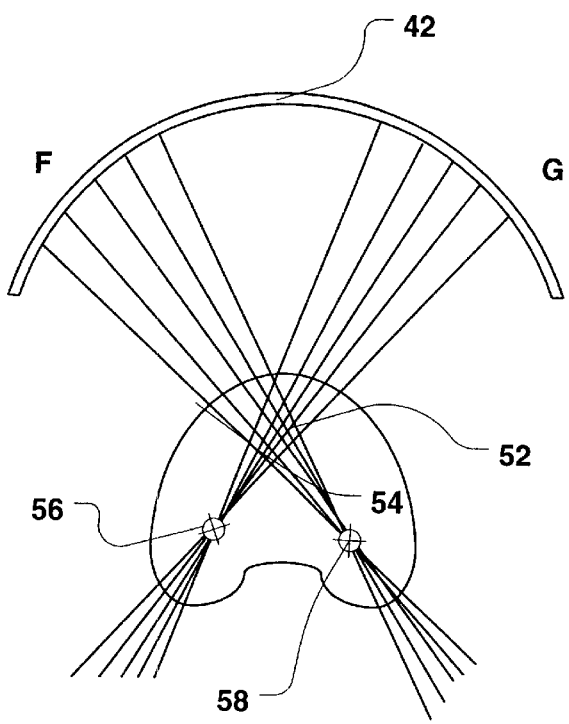
Figure 5A:
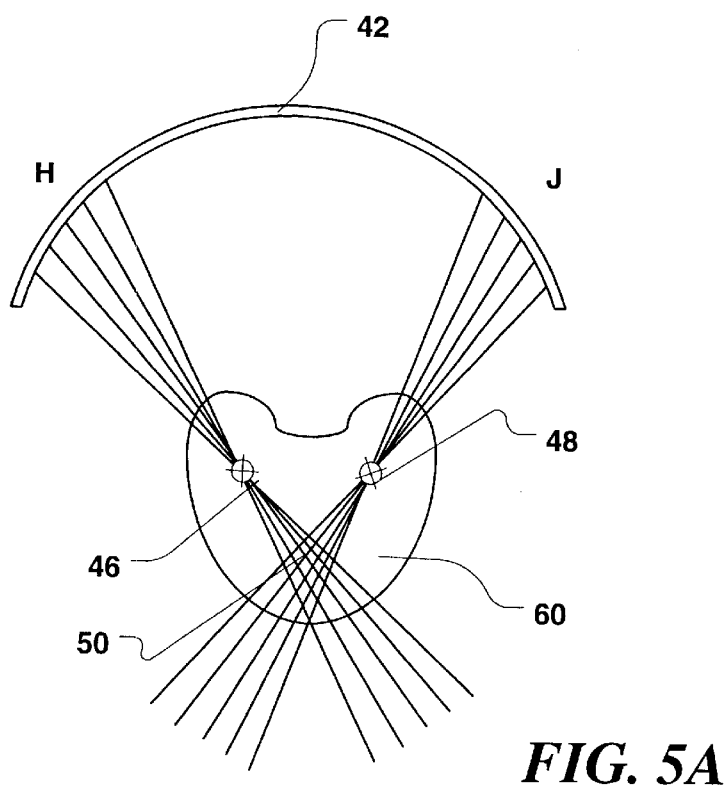
FIGS. 5A and 5B are schematic diagrams of different treatment beam forming techniques used to control the lesion geometry and illustrating spatial-temporal lesion formation.
Figure 5B:
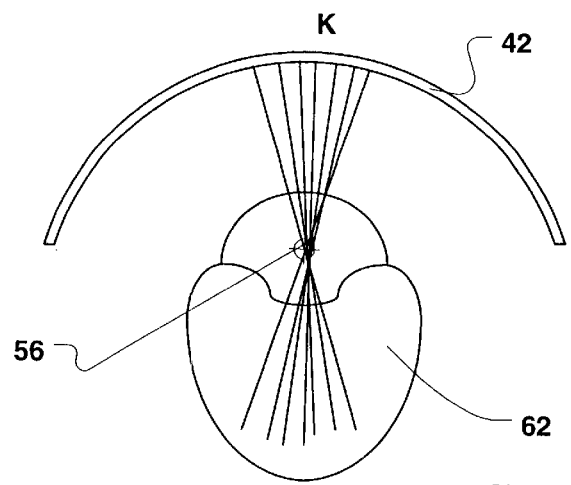

Trans-abdominal ultrasound device 29 shown in FIGS. 3A and 3B has a long shaft 28 that can be inserted into the patient's abdominal cavity through laparoscopic surgery cannula 34, which is disposed in a puncture hole on the abdominal wall. Under visual guidance of a laparoscope, distal end 30 of the device is brought in close contact with the uterine fibroid. As in the trans-cervical device, ultrasound array transducer 36 is preferably mounted at distal end 30 of the device for imaging and therapy. Guided by the ultrasound image, the physician uses the device to necrose the fibroid tissue. The distal end of the device is preferably articulated at a flexible shaft segment 31, as shown in FIG. 3C, with one or two knobs 32 (depending upon whether one or two axes of articulation are provided) that are disposed on handle 33 of the device. This flexible shaft segment permits treatment zone 38 to point in different directions to accommodate different tumor positions. The ultrasound transducer may be disposed in a cover case balloon 41 or other cover at the tip of the device (FIG. 3C).

Cover case balloon 41 is elastomeric and conforms to an outer surface of a tumor, providing more efficient acoustical coupling between the transducer and the treatment area; the curvature of the tumor contour will, in general, be different from the curvature of the ultrasound transducer. Moreover, during a conventional laparoscopic procedure, the patient's abdomen is inflated with $CO_2$ gas to create a large working space. A gas gap between the transducer and the tumor, however, would block the ultrasound transmission. Instead of penetrating into the tumor, the ultrasound beam would be reflected back to the transducer. The therapeutic effect would thus be diminished and the transducer might be damaged by the reflected ultrasound energy.

It thus is important to maintain good acoustic coupling between the treatment tissue and the ultrasound transducer while provide the ultrasound therapy. Water, saline, and most water-based solutions and gels are excellent coupling media. In diagnostic ultrasound imaging, water-based coupling gel is widely used. However, gel may have limitations in trans-abdominal ultrasound therapy for treating uterine fibroids. Unlike skin, the fibroid is much less compressible. It is also more difficult to apply manual pressure during a laparoscopic procedure to conform the fibroid to the surface contour of the transducer. Gel may be used to fill the remaining gaps, but gas bubbles trapped in the gel are difficult to squeeze out.

In this preferred embodiment of the present invention, water-filled cover case balloon 41 (FIG. 3C) is fabricated of thin elastic material and is placed between the transducer and the fibroid to ensure effective coupling of the ultrasonic energy into the tumor mass. Under a small manual pressure, the balloon is conformed to both the transducer surface and the fibroid surface. If the transducer is inside the balloon, only the fibroid surface needs to be wetted with sterile saline to keep a good coupling to the balloon surface. Alternatively, cover case balloon 41 may be fabricated of a semi-permeable membrane material that enables liquid to weep from inside the balloon. The "weeping" of the fluid from the balloon thus can keep the fibroid surface wet during the treatment. When the internal pressure is higher than the pressure in the abdominal cavity, the sterile saline or water inside the semi-permeable balloon readily weeps through the semi-permeable membrane to create a fluid interface-layer that maintains continuous effective coupling.

Figure 11:
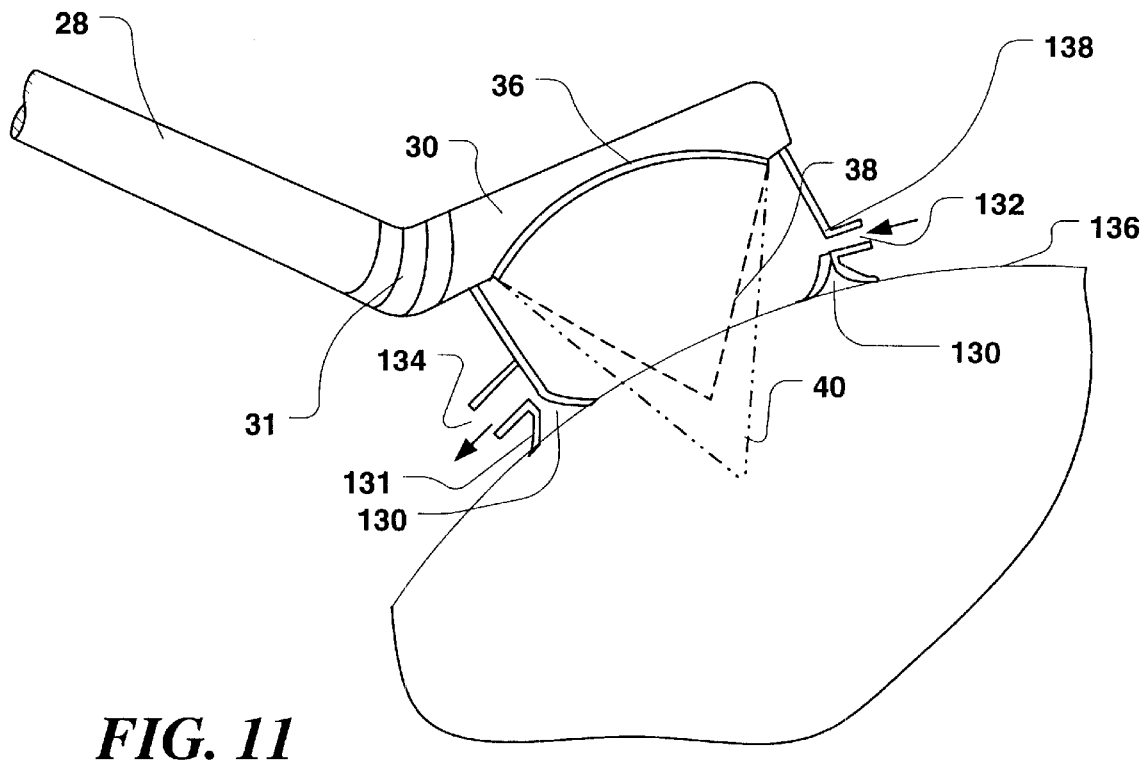
FIG. 11 is a side elevational view of the ultrasound device and a cross-sectional view of a liquid-filled vacuum cap that provides coupling between the fibroid tumor and the ultrasound transducer.

Alternatively, as shown in FIG. 11, a vacuum cap 138 made of soft rubber, plastic, or other elastomeric material, may also be applied at the distal end of the device to provide the acoustic coupling as shown in cross section at FIG. 11. The cap surrounds ultrasound transducer array 36 and is open at its front, opposite the array. The front opening of the cap is large enough to permit the ultrasound beam to pass without obstruction. Around the open end of the cap, a rim 131 has a double lip 130. The double lip is soft and elastomeric and can conform to the shape of a tumor surface 136. A vacuum port 134 is provided in fluid communication with the double lip, and a vacuum source coupled to this port provides a negative pressure within the double lip that holds the cap tightly on the tumor. Sterile water is then provided through a port 132 that communicates with an interior of the cap to provide the acoustic coupling between the transducer and the tumor. The cap works as a wall to block gas from getting into the cap. In case there are any minor leaks, the leaking gas and water are removed immediately at the double lip.

To protect the ultrasound transducer against accidental damage caused by the reflected ultrasound power when there are large gas bubbles or gaps between the transducer and the tumor, or when the device is lifted from the tumor while the high intensity ultrasound output is still on, the present invention preferably uses the ultrasound imaging capability to detect the existence of gas. When a gas gap exists, it causes a strong reflection detected when ultrasound imaging. The reflection may also bounce back and forth between the transducer and the gas gap, resulting in a reverberation (multiple reflections). The strong reflection or reverberation appear(s) as very bright echoes in a large portion of the image. When observing this unique echo image, the medical practitioner may adjust the position or the coupling of the ultrasound device to eliminate the trapped gas. As an alternative, an automatic gas detection technique may be used to avoid the reflection damage. By using the unique characteristics of the gas in the reflected echo signal, the system may detect its existence during the imaging process.

When the strong echo is detected, the system may automatically turn off the high intensity ultrasound output to the area where there are gas gaps. This automatic power shut down process is accomplished almost instantaneously, so that thermal damage to the transducer array is avoided.

During therapy application, the ultrasound transducer generate heat internally. This heat can possibly cause damage or reduce the service life of the transducer array. Moreover, if the transducer array touches the tumor tissue directly, the high temperature of the transducer array can prematurely, or inadvertently, necrose the tissue surface. The high acoustic absorption of the necrosed tissue at the surface would also prevent the ultrasound beam from penetrating deep into the tumor, so that the deep tumor tissue might not be properly treated. It is therefore very important to keep the temperature of the transducer array and at the tissue interface relatively low during the treatment.

Figure 13:
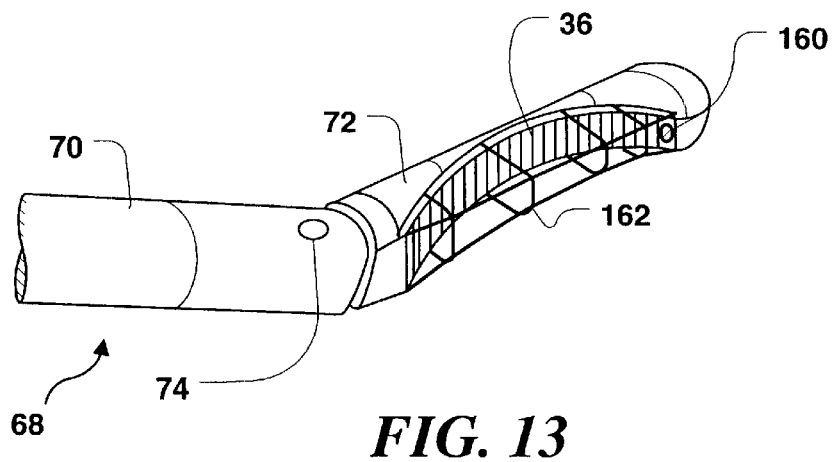
FIG. 13 is an isometric view of a portion of an ultrasound device that includes a structure to maintain a gap between the tissue being treated and an ultrasound transducer array, to convey a coolant liquid.

A plurality of techniques can be employed to cool the transducer array. The simplest approach is to immerse the transducer in water, maintain a gap between the transducer surface and the tumor, and then ensure that the water flows through the gap during the treatment. Two water channels preferably disposed inside the device casing to circulate the cooling fluid may optionally be used for this purpose. The ultrasound transducer array is disposed in one of the channels. Alternatively, both the transducer and the tumor may be immersed in water. In the trans-cervical approach, the uterine cavity is conveniently filled with water. In certain trans-abdominal situations, it may be possible to fill a portion of the abdominal cavity with water. And, in some non-invasive situations it is possible to construct a water dam, sealed at its periphery to the organ surface, creating a water pool in which the applicator may be positioned. As shown in FIG. 13, a thin-wire fence 162 or frame attached to distal end 72 maintains a gap between transducer array 36 and the first interface of patient tissue (e.g., the tumor's outside surface). A variety of such useful standoff structures may be employed, as best suited for the geometric requirements of the application and specific applicator designs. During treatment, a water jet from a port 160 introduces water, or saline, into the gap. Circulation of conditioned water through one or more such ports may be used to control water temperature, pressure, chemical composition, gas content, or volume. Alternatively, the transducer array may be cooled by using a thermal-conductive, acoustic-matching layer (e.g., aluminum) bonded to the piezoelectric ceramic of the ultrasound transducer array. This thermal-conductive layer removes the heat from the transducer ceramic. The heat is removed by water flowing in attached lines or by heat sinks that are connected to the thermal-conductive layer.

To simplify the device design and to reduce the size of the endoscopic instrument, one ultrasound transducer array is used for both imaging and therapy. A concave transducer array provides a good compromise to simplify the design for both functions. Natural focusing of the concave geometry simplifies the ultrasound beam forming, where there is no (or less) phase delay needed, and cross-talk among array elements is less of a problem. Because of the minimum phase delay required, largerelement pitch size can be used. Large pitch size reduces the number of elements in the array and the number of electronic signal channels required. It also helps to reduce the cost of the transducer and the cost of the control unit. Treatment area 38 is geometrically inside imaging area 40 of the array (see FIG. 3B). The entire treatment area is under the ultrasound imaging monitoring—there is no blind spot in the treatment area.

Figure 12:
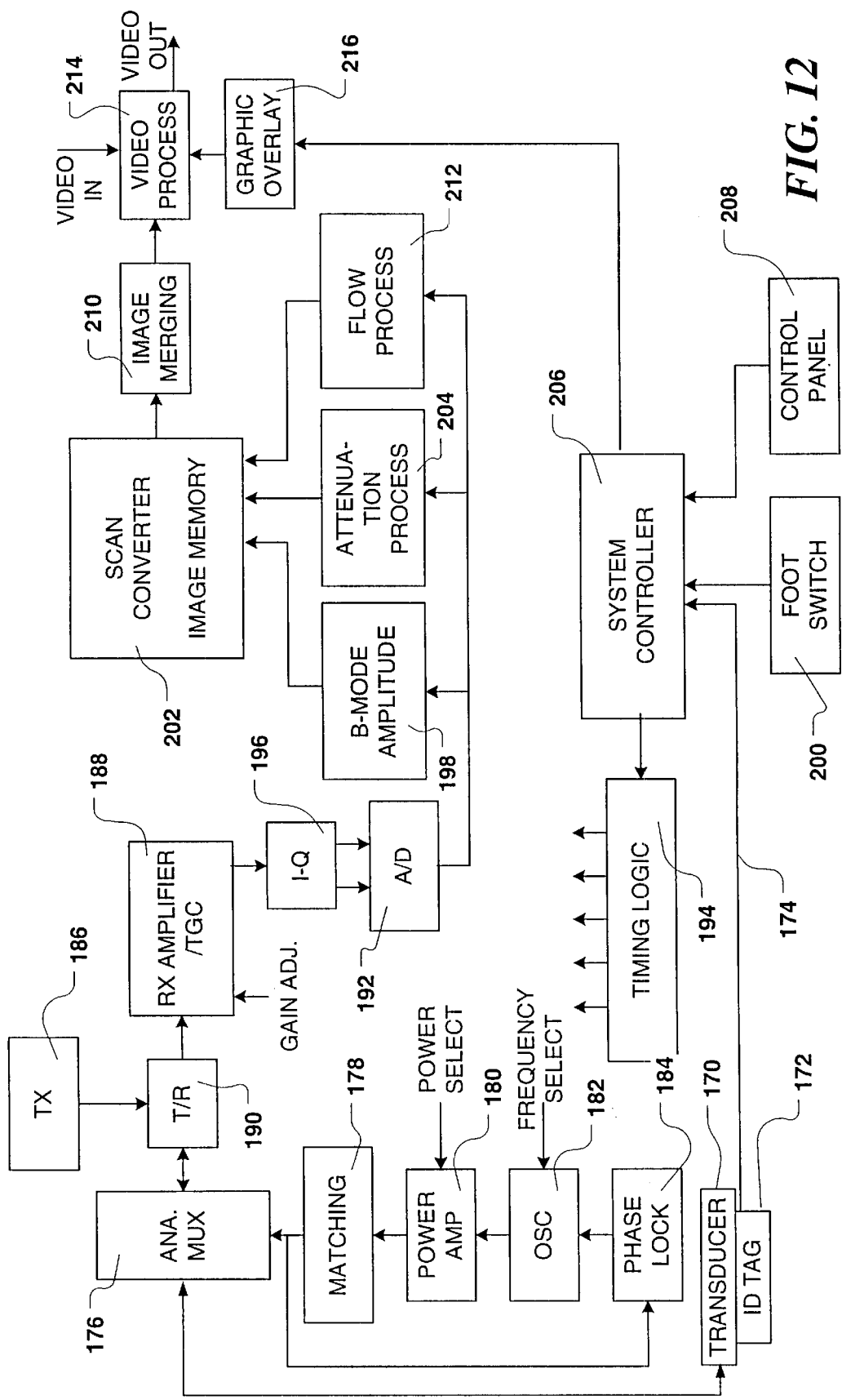
FIG. 12 is a system block diagram of the control electronics in the control unit.

FIG. 12 is a simplified block diagram of the electronic control system according to the invention. The specific applicator device connected to the control system is recognized electronically by a system controller 206, which reads applicator data from a memory device, an ID tag 172. Such data include specific functional and calibration information. A switch matrix 176 connects a concave transducer array 170 to the therapeutic circuitry or to the imaging circuitry. During imaging, an imaging transmitter 186 generates pulse sequences to drive the ultrasound transducer array through a transmit-receive switching matrix 190. The imaging receiver amplifies and processes the echo signals captured by the transducer array. During the therapy phase, switch matrix 176 connects the transducer array to the therapeutic transmitter chain to form and steer a high intensity ultrasound beam within the tissue being treated. To monitor the treatment process, the transducer array may be periodically switch back to the imaging circuitry to form frames of ultrasound images during the treatment.

System controller 206 provides overall control and synchronization of the multiplicity of functions executed by the system including an operator interface control panel 208, a foot switch 200 that is used for initiating and arresting therapy, and a timing logic 194, employed for establishing appropriate phasing of the therapeutic phased array transmit chain. This chain comprises a primary oscillator 182, a phase locked loop 184, a multi-channel power amplifier 180 and matching networks 178. Additionally, timing logic 194 provides data to the imaging chain that includes the receive amplifiers and time-gain compensation circuits 188, a quadrature detection circuit 196, an analog-to-digital conversion circuit 192, an Intensity (B) mode processing circuit 198, an attenuation processing circuit 204, a Doppler flow processing circuit 212, and a scan conversion circuit 202. Images of the target tissue are converted to a format compatible with standardized operating room video display in image merging circuits 210 and mixed with other video sources (e.g., hysteroscopic optical imaging), and user interface graphics, and processed in graphic overlay 216, which is included in a video processor module 214, for display.

Thermally necrosed tissue has a much higher acoustic attenuation (>1.0 dB/cm/MHz) than the untreated tissue (0.4–0.7 dB/cm/MHz). This property may be used to monitor or visualize the treatment area. One technique to measure the tissue attenuation change is to measure the frequency spectral change in the echo signal. High frequency components in the frequency band are attenuated more than the low frequency components. By subtracting the spectrum before the treatment from the spectrum after the treatment, the attenuation change can be measured. If the subtracted spectrum is near zero, it indicates that the tissue where the echo is acquired has not been treated. If the result of spectrum subtraction has a significant slope, it means the tissue attenuation has changed, indicating that this area has been necrosed.

Alternatively, or in combination with this attenuation imaging, elasticity imaging may be employed to assess tissue state before, during, or after ultrasonic treatment. Elasticity imaging, the principles of which are well known in the art, provides a visualization of physical and mechanical tissue properties. Necrosed tissues are stiffer and demonstrate elasticity changes. Treatment endpoints may be manually or automatically controlled (under operator control) by use of elasticity imaging parameters.

As an alternative method of therapy that may reduce the treatment time even further, the patient may be given an injection of ultrasound contrast agent, which is a solution of encapsulated air-containing micro-bubbles that are sufficiently small to circulate safely in the blood and blood vessels. When the bubbles are flowing through the fibroid, they will be hit by the high intensity therapeutic ultrasound. The bubbles enhance the ultrasound heating process at the treatment area and make the treatment more efficient.

As a further alternative method of therapy, cavitation may be utilized as a mechanism for speeding effective treatment. Ultrasound with high acoustic pressure and lower frequency increases the likelihood of stimulating the onset of cavitation. The presence of contrast media or bubbles also encourages cavitation. Cavitation can aggressively disrupt tissue and increase energy transfer for an enhanced heating effect.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An ultrasonic system for the treatment of tissue inside a patient's body, comprising:
   (a) a probe configured to be inserted into a patient's body;
   (b) at least an ultrasonic transducer located at a distal end of the probe and coupled to a power supply which energizes the ultrasonic transducer; said ultrasonic transducer producing a focused beam of high intensity ultrasonic energy; and
   (c) an ultrasound transmissive interface located at the distal end of the probe; said ultrasound transmissive interface comprising an in-vivo, biocompatible cap having an opening disposed opposite the ultrasonic transducer and at least a passage and which is sealingly secured to a surface of tissue; and a liquid disposed between the cap and the ultrasonic transducer.

2. The ultrasonic system of claim 1, wherein the cap comprises a double lipped rim around a perimeter of the cap and the at least a passage is configured to adapt to a vacuum to sealingly secure the cap to the surface of tissue.

3. A method for administering an ultrasonic therapy, comprising the steps of:
   (a) providing at least an ultrasonic transducer that emits a focused high intensity ultrasonic energy when energized;
   (b) positioning the at least ultrasonic transducer proximate an undesired tissue;
   (c) positioning a focal point of the at least an ultrasonic transducer to a distal boundary of the undesired tissue;
   (d) energizing the ultrasonic transducer and applying a sufficient thermal dose of focused high intensity ultrasonic energy to form an initial tissue lesion located at the distal boundary of the undesired tissue;
   (e) initiating pre-focal heating of the undesired tissue to a sufficient temperature wherein at least one acoustic absorption characteristic of the heated undesired tissue is enhanced; and
   (f) using at least one of an f-number, an intensity, and a time of the focused high intensity ultrasonic energy to cause the initial lesion to grow toward the ultrasonic transducer and in at least one other dimension, but not substantially beyond the distal boundary of the lesion.

4. The method of claim 3, further comprising the step of repositioning the ultrasonic transducer to direct the high intensity ultrasonic energy at a different portion of the undesired tissue mass, to achieve the desired shape and size of the necrotic zone.

5. The method of claim 3, wherein the desired shape and size of the necrotic zone are selected so that formation of the necrotic zone substantially deprives the undesired tissue mass of a blood supply, causing the ultimate destruction of the undesired tissue mass.

6. The method of claim 3, wherein the desired shape and size of the necrotic zone are selected to control bleeding at a treatment site.

\* \* \* \* \*